United States Patent
Chatterjee et al.

(10) Patent No.: US 9,528,985 B2
(45) Date of Patent: Dec. 27, 2016

(54) DISCONTINUOUS FLUIDIC SYSTEMS FOR POINT-OF-CARE ANALYTE MEASUREMENT

(71) Applicant: Fannin Innovation Studio, Inc., Houston, TX (US)

(72) Inventors: Dev Chatterjee, Houston, TX (US); Atul Varadhachary, Bellaire, TX (US); Leo Linbeck, III, Houston, TX (US)

(73) Assignee: FANNIN INNOVATION STUDIO, INC., Houston, TX (US)

( * ) Notice: Subject to any disclaimer, the term of this patent is extended or adjusted under 35 U.S.C. 154(b) by 0 days.

(21) Appl. No.: 14/992,370

(22) Filed: Jan. 11, 2016

(65) Prior Publication Data

US 2016/0195523 A1    Jul. 7, 2016

Related U.S. Application Data

(63) Continuation-in-part of application No. PCT/US2015/013097, filed on Jan. 27, 2015.

(Continued)

(51) Int. Cl.
- *G01N 33/543* (2006.01)
- *G01N 21/78* (2006.01)
- *B01L 3/00* (2006.01)

(52) U.S. Cl.
CPC ... *G01N 33/54333* (2013.01); *B01L 3/502715* (2013.01); *B01L 3/502761* (2013.01);
(Continued)

(58) Field of Classification Search
CPC .............. G01N 33/54333; G01N 21/78; G01N 2333/908; G01N 15/0656; G01N 27/745; G01N 35/0098; G01N 33/54326; G01N 33/5434; G01N 2446/00–2446/90; B01L 3/502761; B01L 3/502715; B01L 3/502784; B01L 2300/021; B01L 2200/027; B01L 2300/0848; B01L 2300/0858; B01L 2300/0627; B01L 2300/0861; B01L 2200/0647; B01L 2400/043; B01L 2300/087; B01L 2300/043; B01L 2300/0816; B01L 2200/0668

See application file for complete search history.

(56) References Cited

U.S. PATENT DOCUMENTS

| | | | |
|---|---|---|---|
| 5,147,529 A * | 9/1992 | Lee | B03C 1/01 210/695 |
| 9,372,156 B2 | 6/2016 | Knight | |
| 2005/0013741 A1* | 1/2005 | a'Brassard | B03C 1/288 210/695 |
| 2007/0166835 A1* | 7/2007 | Bobrow | C12Q 1/6834 436/174 |

(Continued)

FOREIGN PATENT DOCUMENTS

WO    WO 2012/041809 A1 *  4/2012

*Primary Examiner* — Christine Foster
(74) *Attorney, Agent, or Firm* — Eric P. Mirabel

(57) ABSTRACT

Disclosed herein are systems and methods for using the controlled movement of magnetic particles using controlled magnetic fields in a fluidic device containing separated fluidic regions to detect analytes in solution by immunoassay, such as an enzyme-linked immunosorbant assay (ELISA) for various medical and scientific applications. In order to achieve sequential exposure to the different chemical environments required in an immunoassay, magnetic particles are driven through fluid-containing chambers separated by air-gaps that may take the form of air bubbles or small open-air separations, for example. Externally controlled magnets coupled to actuators draw the flow of magnetic particles through air-liquid interfaces produced by microfluidic surface tension at the air-gap, washing the particles.

17 Claims, 12 Drawing Sheets

Related U.S. Application Data

(60) Provisional application No. 61/932,200, filed on Jan. 27, 2014.

(52) U.S. Cl.
CPC ........ B01L 3/502784 (2013.01); G01N 21/78 (2013.01); *B01L 2200/027* (2013.01); *B01L 2200/0647* (2013.01); *B01L 2200/0668* (2013.01); *B01L 2200/0673* (2013.01); *B01L 2300/021* (2013.01); *B01L 2300/0627* (2013.01); *B01L 2300/087* (2013.01); *B01L 2300/0816* (2013.01); *B01L 2300/0848* (2013.01); *B01L 2300/0858* (2013.01); *B01L 2300/0861* (2013.01); *B01L 2400/043* (2013.01); *G01N 2333/908* (2013.01)

(56) References Cited

U.S. PATENT DOCUMENTS

| | | | |
|---|---|---|---|
| 2007/0172899 A1* | 7/2007 | Graham | G01N 33/80 435/7.21 |
| 2008/0160639 A1* | 7/2008 | Su | B01F 11/0266 436/526 |
| 2009/0246782 A1 | 10/2009 | Kelso et al. | |
| 2011/0008813 A1 | 1/2011 | Dilleen et al. | |
| 2011/0053289 A1* | 3/2011 | Lowe | B01L 3/5027 436/501 |
| 2011/0137018 A1 | 6/2011 | Chang-Yen et al. | |
| 2012/0014836 A1* | 1/2012 | Dittmer | G01N 33/54326 422/69 |
| 2012/0295366 A1* | 11/2012 | Zilch | B01L 3/502761 436/501 |
| 2013/0183678 A1 | 7/2013 | Haselton | |

\* cited by examiner

O⊀ - MAGNETIC BEADS WITH PRIMARY ANTIBODY

⊚⊀ - SILVER NANOPARTICLES WITH SECONDARY ANTIBODY

◇ - ANALYTE OF INTEREST

- BEAD-BOUND ANALYTE

⚹ - LABELED ANTIBODY

DISCONTINUOUS FLUIDIC SYSTEMS FOR POINT-OF-CARE ANALYTE MEASUREMENT

This application claims priority to U.S. Provisional Patent Application Ser. No. 61/932,200, filed Jan. 27, 2014, which is incorporated by reference herein in its entirety.

BACKGROUND

Technical Field

Embodiments of the field of the disclosure include at least medical devices, medical diagnostics, immunology, cell biology, and molecular biology. In specific embodiments, the disclosure relates to the detection of analyte concentration in solutions prepared from bodily fluids or laboratory samples. The methods and devices in this disclosure are particularly useful for point-of-care medical and laboratory testing in a variety of medical or scientific applications.

Background of the Technology

The present invention relates to a method of detecting analyte concentration based on moving magnetic particles through multiple fluid environments, which are not in significant fluid communication, and are separated by gaseous separations. Specifically, the utility of this invention is to perform immunoassays or other diagnostic assays based on binding events in a rapid, simple, yet quantitative point-of-care testing device. A primary objective of the invention is to eliminate the time-consuming and labor intensive washing steps required to remove unreacted chemicals in conventional immunoassays by taking the reactants out of the solution using magnetic particles, effectively 'washing off' unreacted chemicals left behind in the solution.

In the field of healthcare, many testing devices and methods can be used to perform patient tests required by doctors to make diagnostic decisions. Determining the concentration of analytes in a solution is an essential quantitative parameter for many decisions made by doctors to improve patient outcome. In general, doctors inside or outside of a hospital environment work with other healthcare professionals in the laboratory environment to perform patient tests and determine key quantitative parameters by measuring the concentration of a variety of analytes in various bodily fluids. The immunoassay is one of the most commonly used laboratory tests for determining analyte concentration in the current medical and healthcare environment. Many healthcare situations require immediate determination of test results for the most efficacious treatment decisions. Unfortunately, immunoassays performed in a laboratory environment necessitate delays between sample collection and completion of the test. Point-of-care testing is preferable; as doctors or other healthcare professionals are able to produce rapid testing results for patient care decisions. Additionally, many healthcare environments lack dependable or available laboratory testing facilities or knowledge of laboratory testing methods, necessitating a point-of-care immunoassay device that is rapid, simple to use, and produces quantitative results. Beyond healthcare, immunoassays are required whenever it is necessary to measure the concentration of a protein or other macromolecule in solution. Examples include veterinary applications and detection of toxins in water for environmental monitoring.

Immunoassays are used to quantify the unknown concentration of an analyte within a sample. An immunoassay uses the selective binding of an antibody to the protein of interest to generate a signal and essentially comprises of (i) binding of the protein of interest to its corresponding antibody, and (ii) detecting the extent of this binding. The assays may be semi-quantitative or quantitative. There are two major varieties of immunoassays based on the number of antibodies binding to the analyte: sandwich and competitive. There are several methods to detect the extent of binding. These include enzymatic action on a substrate, fluorescent signals and radioactive signals. A conventional immunoassay, the enzyme linked immunosorbent assays (ELISA), is usually performed in microwell plates, such as 96-well plates).

Prior to detection, it is essential to remove unbound reactants. This is generally accomplished by serial washing (all sandwich ELISA variants). Washing increases the sensitivity of the detection. However, washing increases both the time and complexity of the operation, requiring either expert handling or significant automation cost and complexity. Another form of immunoassay is lateral flow assay (LFA) where the spontaneous flow of fluid along a chromatographic matrix is used to mix the different antibodies and analytes together. LFAs are typically small, quick, point-of-care devices. However, absence of washing during the flow limits the sensitivity and range of the detection process. Currently, there are no methods to do an accurate, quick, cheap, hand-held, point-of-use immunoassay.

Other assays can also be modified to be performed using the general principles of immunoassays. These include (but are not limited to) bioassays for cells (human cells, microorganisms, and other cell types), nucleic acids (mRNA, siRNA and others), and assays for other biomacromolecules.

The general principles of immunoassays may also be used for purposes of purification of biologics, including but not limited to the purification of proteins, DNA, RNA, lipids, or other biological molecules derived from complex mixtures and extracts of cells or tissues.

Magnetic particles are especially constructed to be attracted strongly to applied magnetic fields, but they retain no residual magnetism upon removal of the magnetic field. They are commonly used in immunoprecipitation—a method used to recover analytes of interest from a solution using repeated steps of magnetic precipitation, washing and elution.

Microfluidics is a discipline that deals with the behavior and manipulation of liquids that are geometrically constrained such that surface forces acting on the liquid, like surface tension and fluidic resistance dominate rather than bulk forces, like gravity, which predominate at the macro level. Microfluidics generally depend on the movement of liquid within the constrained spaces. Embodiments of the disclosure encompass methods and compositions that can be employed in a microfluidic form or in a larger fluidic embodiment.

US 2013/0206701 describes a method of transporting magnetic particles between separated fluid compartments in a rotational body that spins about a stationary magnet, using centrifugal forces and magnetic forces to alternate between fluid compartments and empty spaces within the rotational body. Disclosed therein is a rotating fluidic disc that contains both large empty spaces and fluidic regions and is utilized for the transport of magnetic particles through these regions. Presence in a region, though not control of location within a region, is enabled by rotation of the fluidic disc about a fixed magnet, with regions of the rotating fluidic disc designed to regulate particle movement. Currently, there exists no method for transporting magnetic particles between separated fluid compartments by movement of a magnet coupled to actuators relative to a fixed fluidic device as described in the present disclosure.

U.S. 2008/0073546 A1 describes methods of improved mixing by rotational movement in microfluidic structures in the context of magnetic particles located in fluid environments. Magnetic particle mixing patterns can be coarsely controlled by rotational frequency and rotational direction about a magnet.

BRIEF SUMMARY

The present disclosure provides a system and method for determining analyte concentration by means of a device comprising: a container, such as a cartridge or cassette or card, for example, containing fluidic compartments separated by gaseous separations, magnetic particles with attached binding agents for binding analyte, at least one moving magnet external to the cartridge which pulls the magnetic particles through different regions of the cartridge.

Embodiments of the disclosure include methods to perform a point-of-care quantitative assay, wherein the means of performing the assay involves use of magnetic particles in a device. In specific embodiments, the magnetic particles are transferred through different regions of the device by the motion of magnets coupled to actuators such that compositions bound to the magnet are subjected to various assay reactions (for an example, see FIG. 1).

Embodiments relate to a method of detection and/or quantification of entities of interest (such as molecules, cells or microorganisms of interest) in a liquid primarily using the movement of magnetic particles through different regions of a device. The movement may be across static 'pools' of solutions, although fluid movement may be used for detection. In this aspect, the subject matter of the present disclosure differs from all microfluidic devices that primarily work through the flow of liquid through channels. In specific embodiments, the device is utilized in the absence of centrifugal force.

In one embodiment of the disclosure, a method is provided for detecting and quantifying the amount of analyte in a solution using magnetic particles coated with one or more binding agents for the analyte (such as antibodies, including primary antibodies) wherein the magnetic particles are moved under the influence of an external magnetic field across different regions of the device. The binding agent may be an antibody, protein, peptide, or nucleic acid, for example. The binding agent (which may be referred to hereafter as antibodies merely as an example) are specific to the analyte in question; for example, a detection method for a small molecule such as cortisol (a hormone present in blood) will involve the use of anti-cortisol antibodies and an assay for a macromolecule, such as b-natriuretic peptide (BNP) will involve the use of one or more anti-BNP antibodies. The antibodies can be derived from other species (mouse, rabbit, etc.) or of a more humanized form. The antibody may be of any kind, including scFv, monoclonal antibodies or antibody mimetics like affibodies and monobodies.

In a further embodiment of the method, the antibodies (primary antibodies) detect and bind the analyte of interest. In a still further embodiment, a second region inside the device contains nanoparticles/dye/enzyme/other markers in suspension attached to a second variety of antibodies (secondary antibodies), which also bind to the analyte, and a third region which contains at least one detecting chemical, all the regions being separated from one another. In a specific embodiment, the secondary antibodies are attached to an enzyme (e.g., horseradish peroxidase) while the third region contains a chromogenic substrate for the enzyme (e.g., 3,3',5,5'-Tetramethylbenzidine or TMB). In another embodiment of the method, the secondary antibodies are attached to nanoparticles made of silver and the detecting region contains hydrogen peroxide; in a further embodiment the detecting region also contains a dye, whose bleaching under the influence of decomposing hydrogen peroxide is used as a detection and quantification method. In cases wherein an enzyme is employed, the third region may lack nanoparticles such as silver nanoparticles; in such cases, an enzyme performs the function of the silver nanoparticles (or a composition attached to the silver nanoparticles), as both are catalysts that convert chromogenic substrate molecules in a subsequent region of the device. Other embodiments that include variations of these embodiments are also encompassed in the scope of the disclosure.

Detection can be accomplished by various means. In one embodiment of the method, a smartphone camera and program ('app') is used to quantify the change in dye color using an unbleached dye pool as a standard. In a similar way, a combination of a light source and detector inside the device is used to quantify the color change in the dye. In a further embodiment, movement of fluids within the fluidic environment is used as a means of quantifying the reaction magnitude. In one embodiment of the method of detecting and quantifying the amount of analyte in a solution using magnetic particles coated with primary antibodies, the nanoparticles in the second region are made of a material (polymeric, metallic, etc.) non-reactive with hydrogen peroxide, and not having magnetic properties. In another embodiment, these nanoparticles in the second region are coated with catalase along with the secondary antibody. In a further embodiment of the method, the nanoparticles are coated with an enzyme, like horseradish peroxidase, and the detecting region contains the corresponding substrate.

In some embodiments of the method of detecting and quantifying the amount of analyte in a solution using magnetic particles coated with antibodies, the second region contains the secondary antibody conjugated to an enzyme, like horseradish peroxidase, and the detecting region contains the corresponding substrate (e.g., TMB). In a further embodiment, the detection reaction is limited by movement of the magnetic particles out of the detection region after a period of reaction; and in a still further embodiment the detection reaction (e.g., color change of the TMB or other chromogenic solution) is limited by addition of a stop solution.

In one embodiment of the method of detecting and quantifying the amount of analyte in a solution using magnetic particles coated with antibodies, the detecting antibodies are replaced by the analyte, converting the sandwich immunoassay into a competitive immunoassay. For competitive assays, in certain embodiments the silver nanoparticles or the enzymes are conjugated to analyte molecules; for sandwich assays, in certain embodiments the silver nanoparticles or the enzymes are conjugated to the second antibody. In another embodiment, the antigen-antibody reaction is replaced by a different biological detecting mechanism (such as nucleic acid mRNA-siRNA, etc.).

In some embodiments of the method of detecting and quantifying the amount of analyte in a solution using magnetic particles coated with antibodies, the device is of a variety of shapes and sizes, including flat, tubular, capillary or other suitable shapes and designs, but of dimensions and surface characteristics necessary to prevent cross-contamination of the different regions under ordinary conditions of use. In some embodiments of the method of detecting and quantifying the amount of analyte in a solution using magnetic particles coated with antibodies, the magnetic particles are moved across the regions of the device by moving external magnets; and in a further embodiment the magnetic particles are moved across the regions of the device using time- and space-varying electromagnetic fields; in a still further embodiment the magnetic particles are moved across the regions of the device using programmed magnetic fields. In some embodiments of the method of detecting and quantifying the amount of analyte in a solution using magnetic particles coated with antibodies, the sample is introduced into the tube by the withdrawal of a plunger at the other end of the tube; in another embodiment the sample is introduced through a cut hole in the cartridge.

The description of the disclosure as presented above is a broad outline of the features and techniques and is in no way meant to limit the scope of the invention. To better elucidate the device, a detailed description of the disclosure is given below.

In one embodiment, there is a method of detecting and quantifying the amount of analyte in a solution using particles that are moved under the influence of an external magnetic field across different regions of a device. In a specific embodiment, the particles are coated with one or more binding agents. In some cases, the binding agents are antibodies that specifically bind to the analyte being detected. In particular embodiments, one of the regions inside the device comprises nanoparticles in suspension coated with a second variety of antibodies (detecting antibodies), which also bind to the analyte, and a third region that contains a detecting chemical, all the regions being separated from one another. In particular cases, the nanoparticles in the second region are made of silver and the detecting region comprises hydrogen peroxide. In certain aspects, the detecting region comprises a dye, such as one whose bleaching under the influence of decomposing hydrogen peroxide is used as a detection and quantification method. In some cases, a smartphone camera and program ('app') records the change in dye color using an unbleached dye pool as a standard, for example. In some cases, a light source and detector are used to record the detectable change (in color, fluorescence, or radioactivity). In particular embodiments, a ratio of values of blue and red pixels are averaged across each pixel to quantify the change in color.

In specific embodiments, breakdown of a chemical and production of a by-product or resultant product (such as hydrogen peroxide and the production of oxygen) drives the movement of fluids within the device. This is used as a means of quantifying the reaction magnitude, in specific embodiments.

In specific embodiments, nanoparticles in the second region are made of a material (polymeric, metallic, etc.) that is non-reactive with at least certain chemicals (including hydrogen peroxide), and not having magnetic properties. In some cases, the nanoparticles in the second region are coated with catalase and a detecting antibody.

In certain embodiments wherein the nanoparticles in the second region are coated with an enzyme, like horseradish peroxidase, and the detecting region contains the corresponding substrate, like TMB, whose change in color under the action of the enzyme is used as a detection and quantification method.

In some cases, the second region comprises the detecting antibody directly conjugated to an enzyme, such as horseradish peroxidase, and the detecting region comprises the corresponding substrate.

In specific embodiments, magnets utilized in the disclosure are not fixed.

In certain embodiments, magnetic particles are coated with analyte, thereby converting the sandwich immunoassay into a competitive immunoassay.

In some embodiments, the antigen-antibody reaction is replaced by a different biological detecting mechanism (like nucleic acid mRNA-siRNA etc).

In some embodiments, the detection reaction (e.g., hydrogen peroxide decomposition or color change of TMB substrate) is limited by movement of the particles out of the detection region after a period of reaction. In some cases, the detection reaction (e.g., hydrogen peroxide decomposition or color change of TMB substrate) is limited by addition of a stop solution.

In certain embodiments, the structure of the device is of a variety of shapes and sizes, including flat, capillary or other suitable shapes and designs, but of dimensions and surface characteristics necessary to prevent cross-contamination of the different regions under ordinary conditions of use.

In specific embodiments, the magnetic particles are moved across the regions of the device by moving external magnets. Magnetic fields are produced by permanent magnets whose direction is controlled in two dimensions by actuators under manual or automatic control by programmable microcontrollers or computers. In specific embodiments, movement between fluidic regions is controlled by the motion of a magnet in a direction, as described by element 206 of FIG. 9, however exemplary embodiments of the present invention utilize control of motion in two directions in order to achieve superior mixing and to control movement within a particular fluidic region, and to control particle flow through the gaseous separation. Repeated movement of the magnet in a second direction perpendicular to the movement described by element 206 of FIG. 9, results in mixing or rastering of the magnetic particles within a fluidic region. In specific embodiments, maintaining the position of magnet at the top of the well near the gaseous separation while simultaneously moving the position of the magnet across the perpendicular direction regulates particle flow to the correct position to cross the gaseous separation. This method may move across the gaseous separation as described by the dotted line in element 301 of FIG. 10.

In certain embodiments, in order to ensure adequate separation of the particles for maximum exposure to the solvent, the magnet is moved at a very deliberate speed such that: the magnet moves faster than the speed of the magnetic particles in solution, thereby moving ahead; then, the speed of the magnet is reduced to allow the magnetic particles to catch up. As the particles move to the new position of the magnet, the ones that are closer to the magnet move earlier, thus ensuring that all the particles move at different speeds, and hence spread out in the solution. Clumping or aggregation of particles reduces the surface area exposed to the solution, and in embodiments wherein this differential speed is employed, this ensures that the particles do not move as an aggregate. A variety of speeds and stop times of the magnet can be used to get this effect.

In some cases, the magnetic particles are moved across the regions of the device using time- and space-varying electromagnetic fields. In certain cases, the magnetic particles are moved across the regions of the device using programmed magnetic fields.

In some cases, the methods of the disclosure are performed, but the analyte is not detected because it is not present in the sample.

In one embodiment, there is a method of detecting an analyte in a sample solution in a device, said device comprising a plurality of regions, comprising the step of subjecting the sample solution to magnetic particles in the device, wherein said particles comprise a binding agent that binds to the analyte, and wherein the detecting comprises moving the magnetic particles under the influence of an external magnetic field across different regions of the device. The analyte may be a protein, peptide, small molecule, cell, cellular particle, or nucleic acid. The binding agent may be a protein, peptide, or nucleic acid. The binding agent may be considered a first antibody.

In specific embodiments, the analyte is a small molecule and the binding agent is an antibody. In some cases, the analyte is a protein and the binding agent is a first antibody. In particular cases, the analyte is a nucleic acid and the binding agent is a nucleic acid. The analyte may be a mRNA and the binding agent may be a siRNA.

In an exemplary embodiment, the detecting provides quantification of the amount of analyte in the solution.

In particular embodiments, the solution comprises a sample of any bodily fluid from an individual.

An individual subjected to the methods may be in need of point-of-care assaying for the analyte. The individual may be suspected of having a medical condition to which the analyte is indicative. The individual may be suspected of having been exposed to a pathogen.

In some cases, the magnetic particles are coated with one or more binding agents.

In particular embodiments, the plurality of regions of the device are configured in a linear path for movement of the magnetic particles. In some cases, the plurality of regions of the device are configured in a sequential path for movement of the magnetic particles. In some aspects, a first region of the device is configured for loading of the sample solution. In particular aspects, a second region of the device comprises the magnetic particles. A first region of the device may be configured for loading of the sample solution and the first region of the device also may comprise the magnetic particles. A region of the device may comprise nanoparticles or enzymes, said region being subsequent in the sequential path to the region of the device comprising the magnetic particles.

In specific embodiments, nanoparticles or enzymes have attached thereto at least one second antibody that binds to the analyte. In some cases, the nanoparticles or enzymes have attached thereto at least one analyte. In certain cases, the binding agent is a first antibody and both the first antibody and the second antibody bind to the analyte but are nonidentical. The nanoparticles may be comprised of silver. In some embodiments, a region of the device is subsequent in the sequential path to the region of the device that comprises the nanoparticles or enzymes and comprises at least one detecting reagent. Enzymes as described herein may be catalase, horseradish peroxidase, or alkaline phosphatase, for example.

In some cases, at least one detecting reagent comprises hydrogen peroxide. In particular aspects, the breakdown of hydrogen peroxide produces oxygen that drives the movement of the particles along the sequential path in the device. In certain cases, the extent of movement of nanoparticles in the device is used as a means of quantifying the reaction magnitude.

In some embodiments, at least one detecting reagent comprises a dye whose bleaching under the influence of decomposing hydrogen peroxide is detected. A camera may detect at least one detecting reagent. In certain cases, the camera directly or indirectly detects a change in at least one detecting reagent. A detecting reagent may comprise a dye and a smartphone camera and application detect a change in color of the dye. In certain aspects, the change in the color of the dye is compared to unbleached dye pool as a standard.

In certain embodiments, a light source and detector directly or indirectly detects a change in at least one detecting reagent. A detecting reagent may comprise a dye and a light source and detector detect a change in color of the dye.

In some cases, a ratio of values of blue and red pixels are averaged across each pixel to quantify the change in color.

In some embodiments, the nanoparticles are comprised of a material that is non-reactive with hydrogen peroxide. The nanoparticles may be comprised of a polymer or metal. In certain cases, the nanoparticles do not have magnetic properties.

In some embodiments, at least one detecting reagent comprises a chromogenic substrate for the enzyme, such as 3,3',5,5'-Tetramethylbenzidine (TMB), 3,3'-Diaminobenzidine (DAB), or 2,2'-azino-bis(3-ethylbenzothiazoline-6-sulphonic acid) (ABTS).

In specific embodiments, the second antibody is directly conjugated to an enzyme and at least one detecting reagent is the corresponding enzyme substrate.

In particular embodiments, a detection reaction for at least one detecting reagent is limited by movement of the particles out of the region after a period of reaction.

In certain aspects, the detection reaction comprises hydrogen peroxide decomposition or color change of TMB substrate, or one or more other chromogenic substrates. A detection reaction may be limited by addition of a stop solution.

In some embodiments of the device, the structure of the device is flat or capillary in nature. In certain embodiments, the magnetic particles are moved across the plurality of regions of the device by moving external magnets. In some cases, the magnetic particles are moved across the regions of the device using time- and/or space-varying electromagnetic fields or using programmed magnetic fields controlled by linear actuators.

In particular embodiments, the method is further defined as comprising the following steps: subjecting the sample solution to magnetic particles in the device, wherein said magnetic particles comprise a binding agent that binds to the analyte to produce a binding agent/analyte complex; moving by magnetic force the binding agent/analyte complex to a region of the device that comprises nanoparticles or enzymes, wherein said nanoparticles or enzymes have attached thereto at least one second antibody that binds to the analyte to produce a binding agent/analyte/nanoparticle or enzymes complex; moving by magnetic force the binding agent/analyte/nanoparticle or enzymes complex to a region of the device that comprises at least one detecting agent under conditions that directly or indirectly detect the binding agent/analyte complex/nanoparticle or enzymes complex, thereby detecting the analyte in the sample solution.

The following description presents further embodiments of the features of the method herein described. The conception and specific embodiments described here can be used as a basis for modifying and designing other structures for carrying out the same purposes of the present disclosure by those skilled in the art. However, it should be noted that such equivalent constructions do not constitute a departure from the spirit and scope of the disclosure as detailed here. It is to be noted that descriptions of embodiments, both in words or figures, are meant for clarification and description and do not constitute limits to the disclosure.

DETAILED DESCRIPTION

Figure 1:
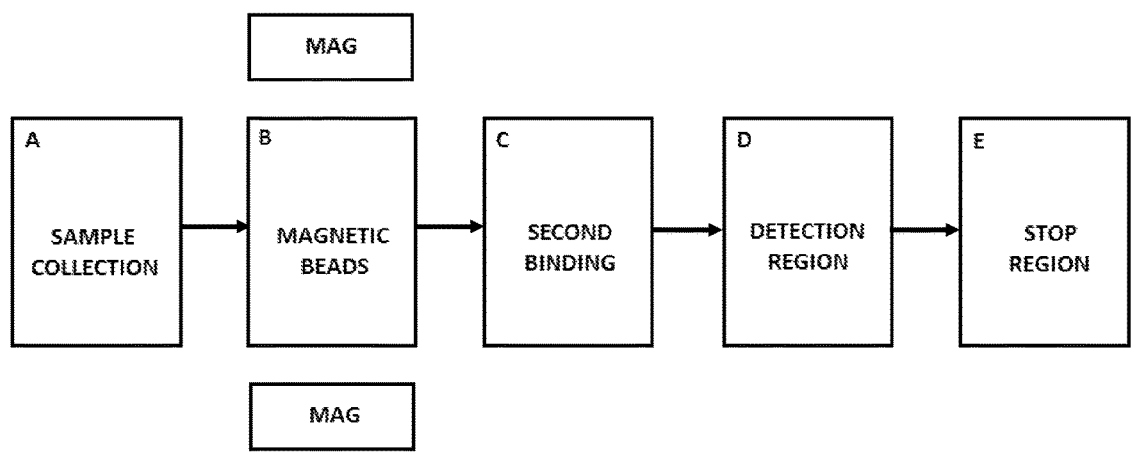
FIG. 1 shows an exemplary embodiment of the device having multiple regions for different aspects of the device and its methods of use.
Regions B to E open only towards each other, but Region A is open to the outside. "MAG." here and all figures represents magnets or magnetic fields. Gaps between Regions A to E are filled with liquid immiscible with the Regions' contents. Regions A & B may be combined into a single region A; Region E may not be present.

Different embodiments and modifications than the ones presented here by one skilled in the arts do not constitute a departure from the spirit and scope of the invention.

I. DEFINITIONS

As used herein, the use of the word "a" or "an" when used in conjunction with the term "comprising" in the claims and/or the specification may mean "one," but it is also consistent with the meaning of "one or more," "at least one," and "one or more than one."

'Analyte' as used herein refers to any entity being detected and/or quantified in the test sample. Often, it is free proteins or proteins bound to surfaces, such as cells or organelles, when the assay is a true immunoassay. However, it can also be other biological macromolecules recognized by proteins (such as steroid hormones or bilirubin) or it can be a completely different biological interaction (such as nucleic acid binding). In many cases, 'analyte' may refer to small molecules that must be measured, and in the present invention any 'analyte' that may be bound to an antibody, protein, nucleic acid, or other binding agent may be used.

The term "binding agent" as used herein refers to a composition that directly or indirectly binds to an analyte. The binding agent may be of any kind, although in certain cases it is an antibody (or another type of protein), peptide, aptamer, or nucleic acid.

'Dye' as used herein refers to any chemical whose change in physical or chemical characteristics can be used as a means of detection and/or quantification of the detection reaction. A dye reaction can also refer to the change wrought in the chemicals of a photographic plate on exposure to different forms of electromagnetic radiation.

Air-gap' as used herein describes the gaseous separations between fluidic compartments and may be comprised of either ambient air or a deliberate preparation of any compositions in the gaseous phase of matter.

'Microfluidic' platform as described here can refer to any embodiment and design of enclosed or open small spaces that possesses the characteristics of the described invention, viz. the separation of the fluidic compartments during ordinary usage. It is a trivial exercise by those skilled in the art to modify the shape and disposition of the compartments from that described below; doing so should not constitute a departure from the spirit of the invention.

'Nanoparticle' or 'particle' as used herein refers to small bits of matter whose dimensions can vary within a wide range but are generally smaller than 1 mm in the largest dimension. It is understood that these terms are not meant to limit the scope of the invention by the vernacular of these terms, and that 'particle' or 'nanoparticle' should be understood to refer to any fluent granular solids.

As used herein, a "point-of-use" device is defined as a device capable of completely performing its stated purpose at the location where it is needed, within a reasonably time-frame. As used herein, "point-of-use" may be interchangeable with "point-of-care".

The disclosure concerns methods and/or compositions for detection of one or more analytes. The detection, in particular aspects, occurs in a situation where a biological sample must be assayed for the presence of one or more particular analytes. In specific embodiments, the analyte in need of detection is known and a device for use in the detection is prepared in advance. The device (or its reagents and structure) may be available in a kit that is suitably packaged for shipping and use. In some cases, the device for detection of the analyte is prepared or modified just prior to its use. In specific aspects, the device is provided with a selection of particular types of reagents to be employed dependent upon the needed purpose. For example, the device may be provided with a selection of binding agents (such as antibodies) and optionally reagent(s) for attachment of the binding agent to magnetic nanoparticles.

In particular cases, the device is employed in a point-of-care situation, where a sample from an individual is in need of being assayed when the individual is present and, in some cases, has freshly provided a sample for analysis. In particular embodiments, the point-of-care situation is in a doctor's office, hospital, airport, combat zone, school, cruise ship, hotel, sports facility or clubhouse managed care facilities, old age homes, nurseries, camps, and so forth. The individual performing the method with the device may or may not be the individual that obtained the sample from the individual. The fluidic device may or may not be disposable following a single use.

II. EMBODIMENTS OF THE DEVICE AND ITS COMPONENTS

Sample

The disclosure concerns analysis of at least one sample from an individual. The individual may provide more than one sample for analysis of the same analyte, and the sample may or may not be the same. In specific embodiments, the sample comprises blood, serum, plasma, urine, saliva, sputum, expectorant, tissue, fecal matter, nipple aspirate, cerebrospinal fluid, ascetic fluids, food extracts, environmental samples, such as river water, drinking water, pool water, ocean water, and so forth. In specific aspects, the sample comprises serum; plasma; cell extracts; supernatants; cell culture supernatants; tissue homogenates, and so forth. In certain cases, the sample is subjected to modification prior to its use in the device, for example to remove material that may interfere with detection of the analyte, to solubilize food matter in water prior to testing, to decant surface water from settled sludge in environmental samples, and so forth. The sample may be diluted prior to entry into the device.

The point of entry of the sample into the device may be of any suitable kind, so long as the sample is loaded so that the analyte may proceed into subsequent regions of the device for methods of analysis. The aperture for sample entry into the device may be of any shape and depth, so long as the analyte may proceed into subsequent regions for methods of analysis. The opening may be round, such as to accommodate a needle, for example.

The sample is present in a solution, in particular embodiments, and the solution may be of any suitable kind so long as the required reactions in the device are able to be performed for detection or quantification of the analyte. In specific cases, the solution is aqueous.

Analytes

The methods and compositions of the disclosure provide analysis of at least one analyte. The analysis may include qualitative detection of the analyte from a sample or quantitative detection of the analyte from a sample. The analyte may be a biological molecule for which an individual is suspected of having in vivo, and a sample provided by the individual is tested for the analyte. In specific cases, the presence or absence of the analyte provides information about the health of the individual. In particular embodiments, the presence or absence of the analyte is used in diagnosis and/or prognosis of a medical condition for the individual. In some cases, the presence or absence of the analyte provides information whether or not an individual was exposed to a particular biological entity, such as exposed to a certain pathogen (bacterial, viral, prionic, fungal, etc.). The analyte can be an environmental toxin found in seawater (like brevetoxin), or groundwater (like contaminating chemical sludge).

In some cases, the presence of the analyte is indicative of the presence of a disease. The disease may be of any kind. The medical condition may or may not be pathogenic. The presence of the analyte in the sample may be detected such that it is determined that the analyte is systemic in the individual or localized in the individual. The analyte may be an antigen associated with a particular medical condition.

The analyte molecule itself may be of any kind, including at least a cell, small molecule, microorganism, nucleic acid, protein, peptide, glycoproteins, lipoproteins, bilirubin, and so forth. The analyte may be a salivary marker, blood marker, and so forth. Examples of small molecules include cortisol (increased cortisol levels are associated with Cushing's syndrome and adrenal tumors, while decreased cortisol levels are associated with adrenal insufficiency (e.g., Addison's disease) and adrenocorticotropic hormone (ACTH) deficiency.)

Examples of analytes include cytokines (chemokines and growth factors); kinases and inhibitors; transcription factors; neuro proteins; hormones, etc.

In some cases, the analyte provides information about pregnancy, so in some cases the device is a home pregnancy kit, such as one that detects the pregnancy marker human chorionic gonadotropin. Other applications could tests that measure levels of CK-MB to assess heart disease, insulin to assess hypoglycemia OR prostate-specific antigen to detect prostate cancer, for example. The analyte may provide information about the presence of an illegal substance(s) in an individual, such as narcotics. The analyte may provide information about the presence of prohibited compositions for athletes, such as recombinant human growth hormone (rhGH, rGH, hGH, GH), for example.

Specific examples of analytes include Akt, APO-1, c-Jun, c-Kit, c-Met, CD23, CD26, CD30, CD40, CREB, CRP, caspase-3, GM-CSF, IFN-$\gamma$, IL-1$\beta$, IL-2, IL-4, IL-5, IL-6, IL-8, IL-10, Eotaxin, FGF-basic, G-CSF, GM-CSF, HGF, IFN-$\alpha$, IFN-, IFN-$\gamma$, IL-1$\beta$, IL-1RA, IL-2, IL-2R, IL-4, IL-5, IL-6, IL-7, IL-8, IL-10, IL-12, IL-13, IL-15, IL-17, IP-10, MCP-1, MIG, MIP-1$\alpha$, MIP-1$\beta$, RANTES, TNF-$\alpha$, VEGF, EGF, EGFR, ERK 1/2, Estradiol, FAK, GDNF, GSK-3$\beta$, HGF, HGH, HSP27, Her2, Histone H3, I$\kappa$B$\alpha$, insulin, leptin, MMP-3, MMP-9, MMP-13, p21, p38, p27, p53, p70-S6K, PARP, PRAS40, Rb, IR, IRS-1, IgG1, IgG2, IgG3, IgG4, JAK2, JNK 1/2, SAA, STAT1, STAT3, STAT5a/b, TGF-$\beta$1, TIMP-1, TNF, VCAM-1, VEGF, or a combination thereof.

Magnetic Particles

Any particles possessing the ability to be moved by an external magnetic field can be used for this assay. In one embodiment, the magnetic particles used herein are superparamagnetic particles, which exhibit the property of strong magnetism in a magnetic field but lose all magnetic properties with removal of the field. Most frequently, they are made of uniform polymeric beads that have been coated with a ferric compound. An example of a commercially available (such as Invitrogen or Fisher Scientific) magnetic bead used in the presented embodiment is described [Neurauter A A, 2007]. The magnetic particles are generally of a uniform diameter, varying from a few hundred nanometers to a few microns. In the presented example, magnetic particles of 2.8 microns have been used. Particular ranges include, for example, 200 nanometers to 5 microns, 200 nanometers to 4 microns, 200 nanometers to 3.5 microns, 200 nanometers to 3 microns, 200 nanometers to 2.5 microns, 200 nanometers to 2 microns, 200 nanometers to 1.5 microns, 200 nanometers to 1 micron, 300 nanometers to 5 microns, 300 nanometers to 4 microns, 300 nanometers to 3.5 microns, 300 nanometers to 3 microns, 300 nanometers to 2.5 microns, 300 nanometers to 2 microns, 300 nanometers to 1.5 microns, 300 nanometers to 1 micron, 400 nanometers to 5 microns, 400 nanometers to 4 microns, 400 nanometers to 3.5 microns, 400 nanometers to 3 microns, 400 nanometers to 2.5 microns, 400 nanometers to 2 microns, 400 nanometers to 1.5 microns, 400 nanometers to 1 micron, 500 nanometers to 5 microns, 500 nanometers to 4 microns, 500 nanometers to 3.5 microns, 500 nanometers to 3 microns, 500 nanometers to 2.5 microns, 500 nanometers to 2 microns, 500 nanometers to 1.5 microns, 500 nanometers to 1 micron, 600 nanometers to 5 microns, 600 nanometers to 4 microns, 600 nanometers to 3.5 microns, 600 nanometers to 3 microns, 600 nanometers to 2.5 microns, 600 nanometers to 2 microns, 600 nanometers to 1.5 microns, 600 nanometers to 1 micron, 700 nanometers to 5 microns, 700 nanometers to 4 microns, 700 nanometers to 3.5 microns, 700 nanometers to 3 microns, 700 nanometers to 2.5 microns, 700 nanometers to 2 microns, 700 nanometers to 1.5 microns, 700 nanometers to 1 micron, 800 nanometers to 5 microns, 800 nanometers to 4 microns, 800 nanometers to 3.5 microns, 800 nanometers to 3 microns, 800 nanometers to 2.5 microns, 800 nanometers to 2 microns, 800 nanometers to 1.5 microns, 800 nanometers to 1 micron, 900 nanometers to 5 microns, 900 nanometers to 4 microns, 900 nanometers to 3.5 microns, 900 nanometers to 3 microns, 900 nanometers to 2.5 microns, 900 nanometers to 2 microns, 900 nanometers to 1.5 microns, 900 nanometers to 1 micron, and so forth.

In some cases, the magnetic particles are modified. Such modifications may include the attachment of one or more layers (which may be referred to as coats) with a particular chemical. Such a modification may facilitate binding of an antibody, for example. Thus, in some aspects, the magnetic particles come in a variety of chemical coats that aid the attachment of antibodies. Some of the examples include Protein A, Protein G, streptavidin, etc. A present embodiment uses Protein G-coated magnetic particles as an example. It should be noted that when an analyte is not a protein (or a cell or organelle whose membrane protein is being targeted), a different coat may be used for the particular binding molecule. For example, if the device is being used for a nucleic acid detection or quantification, the detecting nucleic acid may be bound to the surface of the particle using conjugation chemistry principles (e.g., amide bond formation, click chemistry, etc.) and not Protein G.

In particular embodiments, the magnetic nanoparticle is attached to another composition. The composition may be used also for magnetic forces or the composition may be a binding agent, such as an antibody, including an antibody that binds to one or more analytes, for example.

Detection Reagents

The methods and device of the disclosure utilize one or more detection reagents for quantification or qualification of the analyte. The detection reagent(s) may provide the detection directly or indirectly. In particular embodiments, a secondary antibody is attached to another entity, and in some cases the secondary antibody has a detectable marker or has a molecule that is the substrate for a detectable reaction. The secondary antibody binds the analyte, in specific aspects.

In particular embodiments, a secondary antibody used for detection of the analyte (bound to the primary antibody) is attached to another entity that is a nanoparticle or that is an enzyme. In some cases, two or more secondary antibodies are bound per nanoparticle. The nanoparticles (which may be present in the second region of the device) are comprised of a material (such as polymeric, metallic, etc.) that is non-reactive with particular chemicals, such as a substrate of an enzyme used in the detection, including hydrogen peroxide, and do not have magnetic properties. In another embodiment, nanoparticles in the second region of the device are coated with an enzyme (such as catalase) along with the secondary antibody. In a further embodiment of the method, the nanoparticles are coated with an enzyme, such as horseradish peroxidase, and the detecting region comprises the corresponding substrate.

Figure 2:
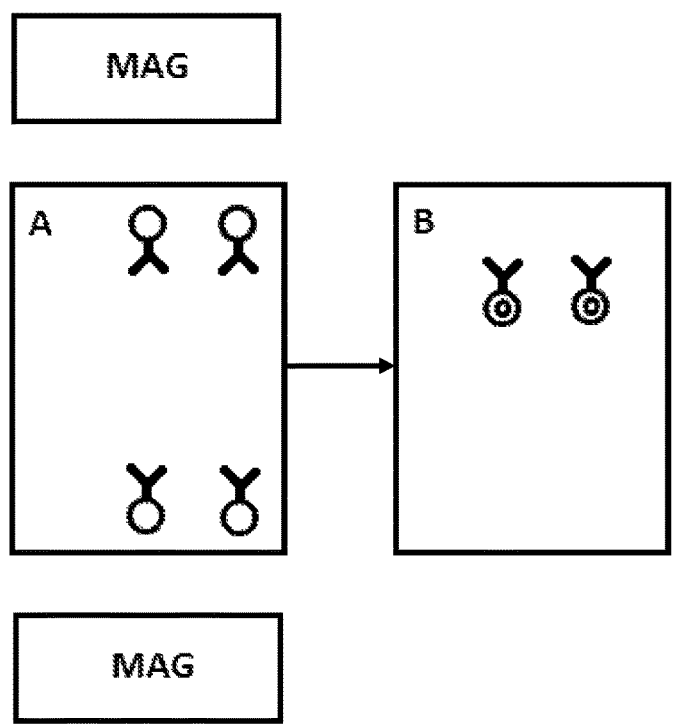
FIG. 2 depicts magnetic beads with primary antibody in Region A; beads or nanoparticles coupled with a secondary antibody in Region B; where Region C is a detection region (containing e.g., hydrogen peroxide), which magnetic beads can be drawn into.
Figure 11:
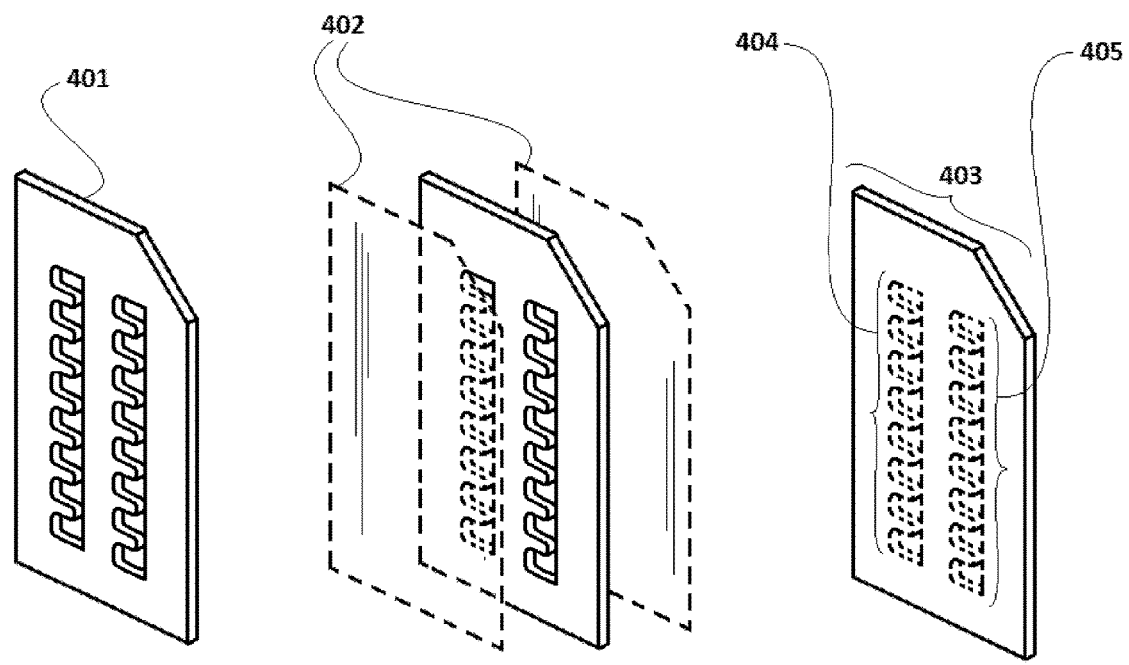
FIG. 11 shows illustrations of the construction and design of a self-contained cartridge for maintaining multiple parallel discontinuous microfluidic systems with flat and transparent sides for the movement of granular solids and subsequent monitoring of microfluidic chambers according to embodiments of the present disclosure.

As noted in brief above, two major varieties of immunoassays are sandwich and competitive. In the sandwich assay, the secondary antibody can be attached directly to a molecule that can trigger the change in the detecting chemical. An example is the binding of the secondary antibody to the horseradish peroxidase enzyme. In that embodiment the detection region contains the chromogenic substrate for the enzyme, commonly TMB. The antibody-bound peroxidase enzyme is thus transported to the detecting region and triggers a color change that is quantified. The secondary antibody can also be bound to metallic (such as silver) nanoparticles instead of enzymes The nanoparticles may be very small (in tens of nanometers). Silver nanoparticles are strongly reactive to all forms of proteins. When used in the sandwich assay, the nanoparticles are coated with the detecting antibody (see, for example, FIG. 2). For the competitive assay, the enzyme or the nanoparticles are coated with the analyte being detected. In the competitive assay, the first region (or chamber) holds the antibody bound magnetic particles and the second region holds the enzyme conjugated to analyte (not from the sample). Therefore, effectively, the analyte molecules in the sample compete with the enzyme bound analyte molecules to bind to the antibody on the particles. If there are more analyte molecules in the sample, these bind to the antibody and less enzyme-conjugated-analyte gets bound. On the other hand, if less analyte molecules are present in the sample, more antibody molecules are open for binding, and more enzyme-conjugated-analytes can bind to them. FIG. 11 shows one particular embodiment of cartridges made of middle layer (401) enclosed in a top and bottom layer (402) with 2 sets of compartments (404 and 405) to create a complete cartridge for use (403). The present disclosure provides methods for the construction of an exemplary embodiment of the discontinuous fluidic system. As shown in FIG. 11, a single piece of any material, including some plastic or polymer, 401 is cut to form the interior of regions within the fluidic cartridge. The fluidic system is closed by the adhesion of two, flanking windows 402 composed of any material, including some plastic or polymer, where at least one window is transparent to at least some forms of light. With a non-interfering adhesive, a complete cartridge 403 is formed comprising multiple parallel fluidic systems 404 and 405. Additionally, the present invention allows the gaseous separations to take the form of any fluid immiscible with the flanking fluidic compartments.

Figure 9:
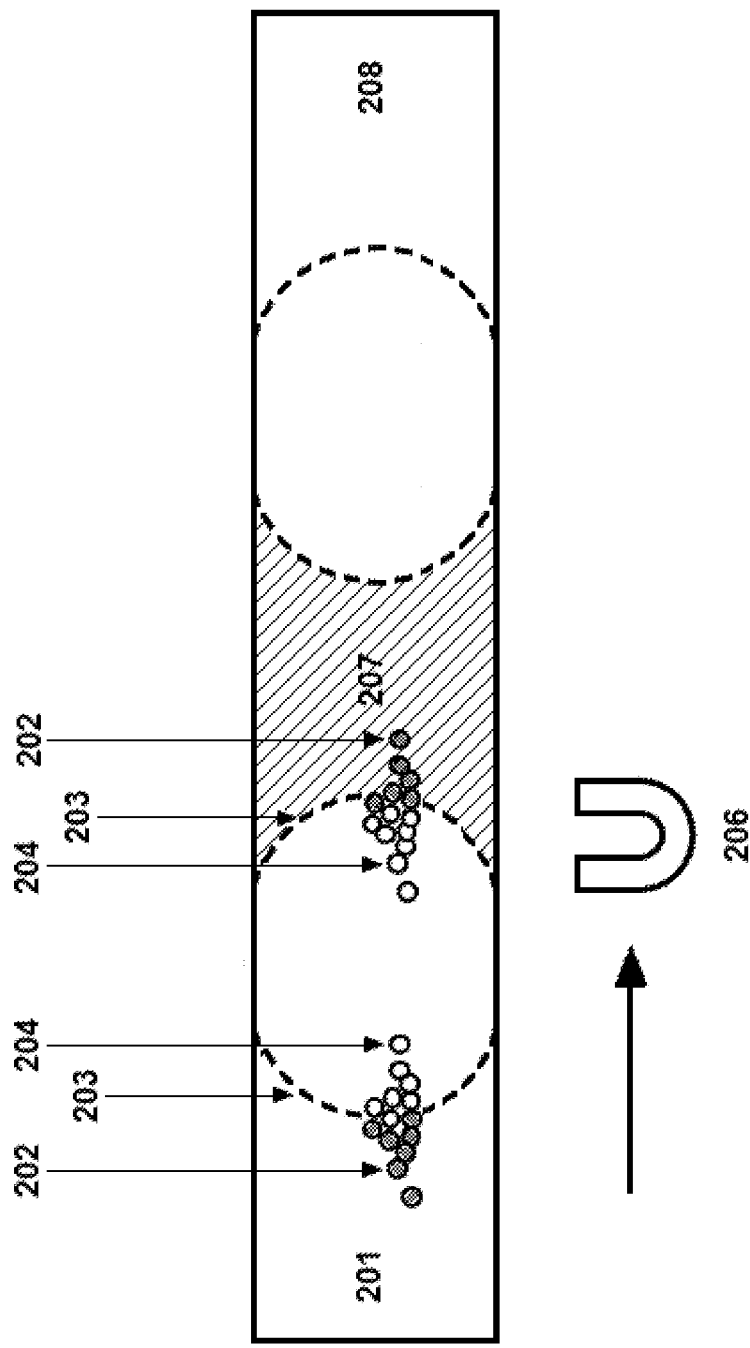
FIG. 9 shows a schematic representation of a discontinuous microfluidic system for rapidly moving magnetic particles through chemical environment steps of the immunoassay. Microfluidic chambers are separated by gaps of air that are stabilized by the forces of surface tension, and magnetic particles move through these gaps of air through external actuation of magnets according to embodiments of the present disclosure.

One example of each method (enzyme and nanoparticles) is illustrated in FIG. 9 and described below.

The detection region of the device may contain a variety of dyes and chemicals (such as PNPP (p-Nitrophenyl Phosphate), ABTS (2,2'-Azinobis [3-ethylbenzothiazoline-6-sulfonic acid]-diammonium salt), OPD (o-phenylenediamine dihydrochloride), TMB (3,3',5,5'-tetramethylbenzidine)] depending on the method chosen. In a particular example herein, hydrogen peroxide is placed in the detecting region when using nanoparticles, and TMB is used when employing the horseradish peroxidase enzyme.

As noted above, a variety of shapes, sizes and materials can be used to construct the device itself. In the example presented, a flat card-like object may be used that contains depressions containing the chemicals with channels connecting the areas. The whole card may be covered (such as with an optically clear material) that keeps the chemicals in the chambers while allowing the detection of the color (or fluorescence or radioactivity) change. The cartridge can also be labeled with an identifier such as bar code or a QR code. In another example, a polymeric capillary (with an internal diameter of 2 French or about 330 microns) is used as the primary structure. Either Teflon or polyethylene may be used as the material of the card or capillary, in specific embodiments.

In the card embodiment, the chemicals may be preloaded in the chambers. The sample chamber can be accessed through a sealable access point (such as a hole) to load the sample into the card. A neodynium permanent magnet of Br-max of approximately 4500 Gauss may be used to move the particles. In the capillary example, a metallic wire (28 American Wire Gauge) is used as the plunger. It may be lightly greased with mineral oil and inserted into the capillary, in some cases.

III. EMBODIMENTS OF METHODS OF USE

Figure 8:
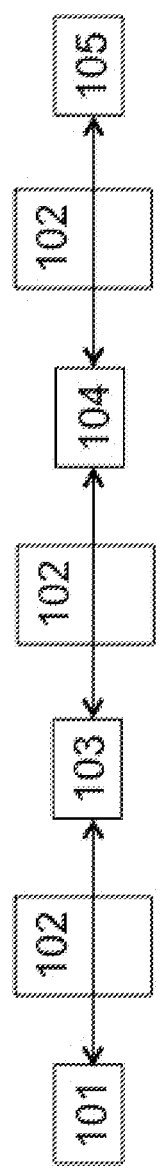
FIG. 8 shows a schematic of a fluidic system where liquid environments are separated by gas environments, generally gaps of air, creating a discontinuous fluidic system according to embodiments of the present disclosure.

The device and methods of the disclosure may be used in a variety of ways for detection of one or more analytes. In some cases, the device is employed in a sandwich immunoassay, whereas in others the device is employed in a competitive assay. Other variations include the number of chambers with specific functions, the type of detection reagents, the specific primary and secondary antibodies being used, and so forth. In some cases the device is a card-like object having channels, whereas in other cases the device is a capillary tube. In FIG. 8, there is an example of a schematic diagram of an embodiment of a cartridge that may be employed for detection of one or more analytes. The regions shown by the numbers 101, 103, 104 and 105 are fluid compartments separated by air gaps 102. The fluid compartments can contain different liquids including sample, antibodies, chemical substrates and magnetic particles. The bi-directional arrows show the possible movement of magnetic particles across the fluid chambers under the influence of an external magnetic field. Thus, in embodiments of the present disclosure, there is a fluidic system in which fluidic and microfluidic systems are comprised of moving fluids where different regions through a channel are in fluidic communication. Instead, the present invention describes a specific fluidic system comprising fluidic compartments that are not in fluid communication. Fluid communication is interrupted by discontinuities, represented by 102 in FIG. 8, that take the form of gaseous separations, producing discontinuous fluidic systems that are instead traversed by particles under some external control. Flanked by at least one fluidic region, as described by the orientation of 101 and 102, and in general are located between two fluidic regions, as described by the orientation of 101, 102, and 103. these gaseous separations form gas-liquid interfaces in the present invention.

Figure 3:
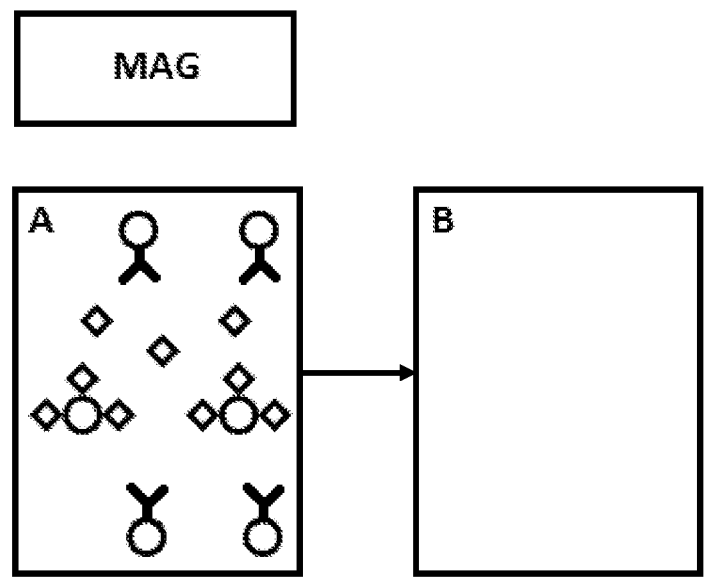
FIG. 3 depicts a competitive assay scheme, where in Region A, analyte is free in solution and is also bound to beads. Analyte is bound by the labeled antibody depicted in Region A, followed by a detection reaction in Region B—where the labeled magnetic beads are drawn in and the bead-bound antibody is detected.
Figure 3:
Figure 4:
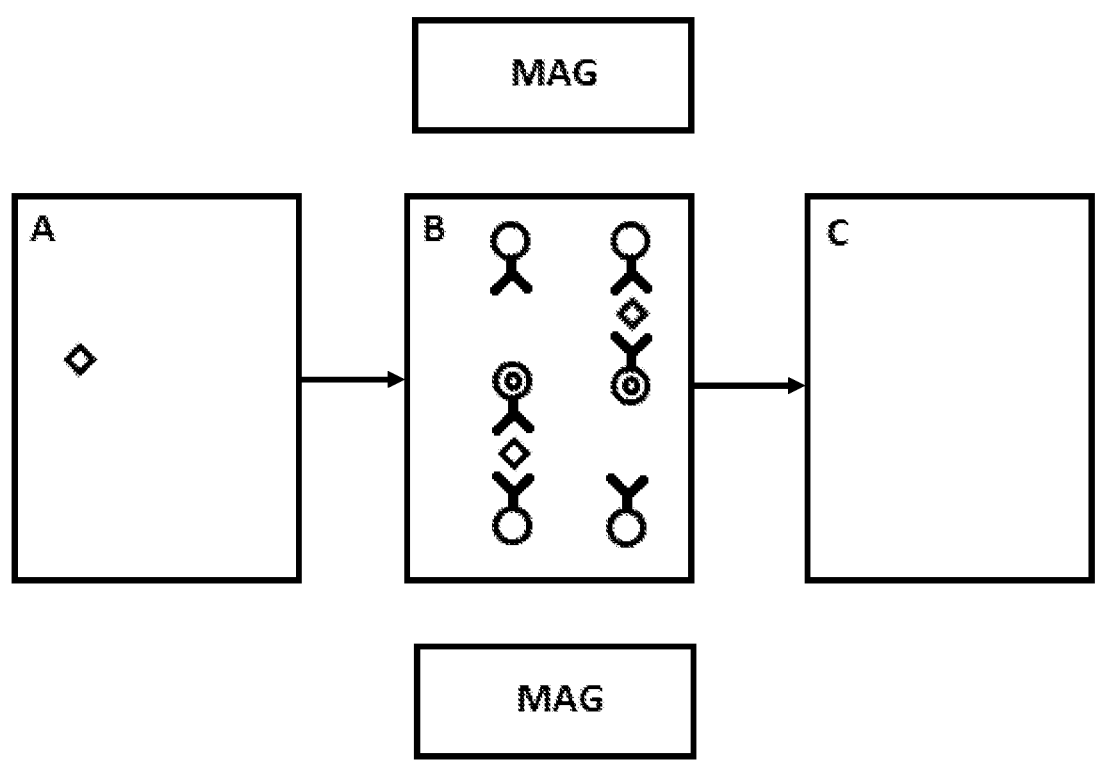
FIG. 4 depicts an analyte binding to both a primary and secondary antibody, where the secondary antibody can be labeled.

In particular aspects of the disclosure, a sample is provided to the device, and the sample thereby may enter a region that has or does not have magnetic particles with a primary antibody. The magnetic particles may be moved into a sample region. Once the sample is in the region with the magnetic particles, the analyte from the sample, if present in the sample, is able to bind to the antibody on the magnetic particles (see FIGS. 3 and 4). In at least some cases there is a need to ensure adequate separation of the magnetic particles for maximum exposure to the solvent. One method of doing so employs movement of the magnet at a deliberate speed. In at least some cases, for short durations the magnet moves faster than the speed of the magnetic particles in solution, and therefore the magnetic particles lag behind the magnet. Once the magnet stops/slows down, the magnetic particles move to 'catch up' with the new position of the magnet. In doing so, the magnetic particles move at different speeds, with those that are closer to the magnet moving earlier. This ensures that all the solution particles move at different speeds. This spreads the magnetic particles out in the solution. Because clumping or aggregation of the magnetic particles can reduce the surface area exposed to the solvent, this differential speed ensures that the solution particles do not move as an aggregate. A variety of speeds and stop times of the magnet can be used to get this effect.

FIG. 9 shows a schematic of an embodiment of the movement of magnetic particles across fluid compartments. Three fluid compartments are shown (201, 207 and 208), shaded differently to represent different composition of the solutions. Element 203 represents the air-liquid interface. Element 202 shows the magnetic particles in the first fluid compartment. Under the influence of an external magnetic field, the particles cross the air-liquid interface (203) and enter the air gap. The particles in the air gap (204) are dragged across the gap using external magnetic fields to reach the next air-liquid interface, which they eventually cross to enter the next fluid chamber. Movement across the air gap essentially 'washes' the particles from non-reacted chemicals in the previous fluid compartment. Thus, n exemplary embodiments, gas-liquid interfaces are useful to the functionality of the present disclosure. Gas-liquid interfaces formed at the interface of fluidic compartments and gaseous separations provide stable separations between fluidic compartments, enabling the use of heterogeneous liquid environments in one continuous fluidic or microfluidic system. Heterogeneous fluid environments in a single fluidic system are described by shading of 201, 207, and 208 (FIG. 9). Steps of numerous industrial processes, chemical syntheses, and biomedical assays, for example, require the exposure of some solid-phase material to a number of different fluidic environments, including but not limited to buffers, solvents, mixtures, aqueous solutions, lipids, colloids, or other fluid environments. In embodiments of the present invention, gas-liquid interfaces are breached (203) and crossed by magnetic particles, or other any particles and granular fluent solids under external control. As depicted in FIG. 9, magnetic particles 202 in fluid 201 pass through air gap 203 to remove contaminating fluids from magnetic particles as in 204, prior to their exposure to the next fluidic environment 207. Simply put, said passage through gas-liquid interfaces serves the same purpose as a washing step in a process or assay. In exemplary embodiments, gas-liquid interfaces exist on either side of an elongated gaseous separation, for example an ovoid air bubble, or simply two gas-liquid interfaces on either end of one elongated pathway flanked by fluidic compartments. Magnetic particles are pulled through at least one gas-liquid interface with minimal fluidic communication between fluidic environments. In exemplary embodiments, said gas-liquid interfaces are curved by the forces of surface tension, in particular volumes found in microfluidic applications. The shape of the gas-liquid interfaces are primarily determined by the absolute volumes or relative volumes of fluids that comprise the interface and the material of the surface which forms the fluidic system. Gas-liquid interface curvature is also determined by the composition of the fluidic environments, and the composition of the gaseous separation. In exemplary environments, the shape of the gas-liquid interfaces are manipulated in order to increase the stability of the gaseous separation by increased surface tension, or to fit into fluidic structures with curved shapes.

In exemplary embodiments, gaseous separations (203) are in a linear arrangement, depicted in FIG. 9, with respect to the fluidic compartments they separating. The present invention allows a method for the exceptionally rapid exposure of solid-phase materials through heterogenous or homogenous fluidic compartments. Embodiments of the present invention utilize permanent magnet control of magnetic particles in multiple dimensions, like the particles in 301. However, in a linear embodiment motion of a magnet in a single linear direction would be sufficient, an exemplary embodiment of which is depicted in FIG. 9.

Figure 10:
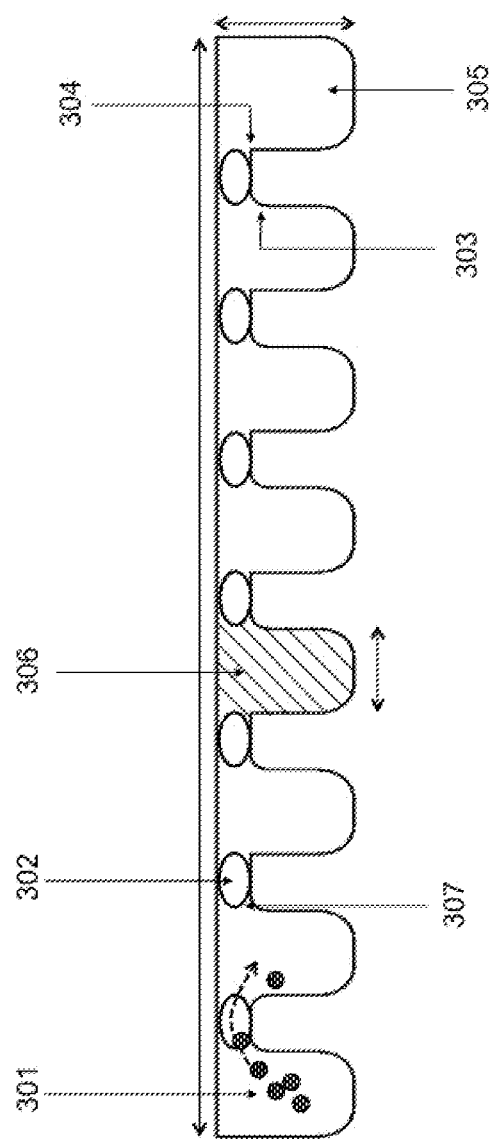
FIG. 10 shows an illustration of an exemplary functional unit of the discontinuous microfluidic system where liquid environments are individual wells separated by comparatively smaller air gaps that sit atop walls that form narrow openings at the top of separating walls with sloped edges to promote unidirectional particle flow.

FIG. 10 shows a particular embodiment of a series of fluid compartments (301) separated by air gaps (302). The edges of the fluid compartments may be specifically rounded at one edge (303) but not the other (304) to aid transfer of particles. The embodiment also represents compartments of different sizes (305 and 306) to accommodate different volumes of liquid. In exemplary embodiments, gaseous separations are formed naturally without requiring explicit methods to add gas. In these embodiments, air-gaps are located in small channels at the top of fluidic compartments, depicted in FIG. 10 as 302, and fluidic compartments are filled from the bottom. The present invention describes methods for using a system-specific known volume of liquids to produce a gaseous separation of known volume within channels between fluidic compartments as a result of gravity and surface tension. In exemplary embodiments, directionality of particle flows are regulated by the shape of the bottom surface of gaseous separations. Utilizing a rounded edge 303 at the entry point of an air gap 302 allows magnetic particles to concentrate at the gas-liquid interface 307. Conversely, a right-angle 304 directs magnetic particles to exit easily into the next chamber.

Figure 5:
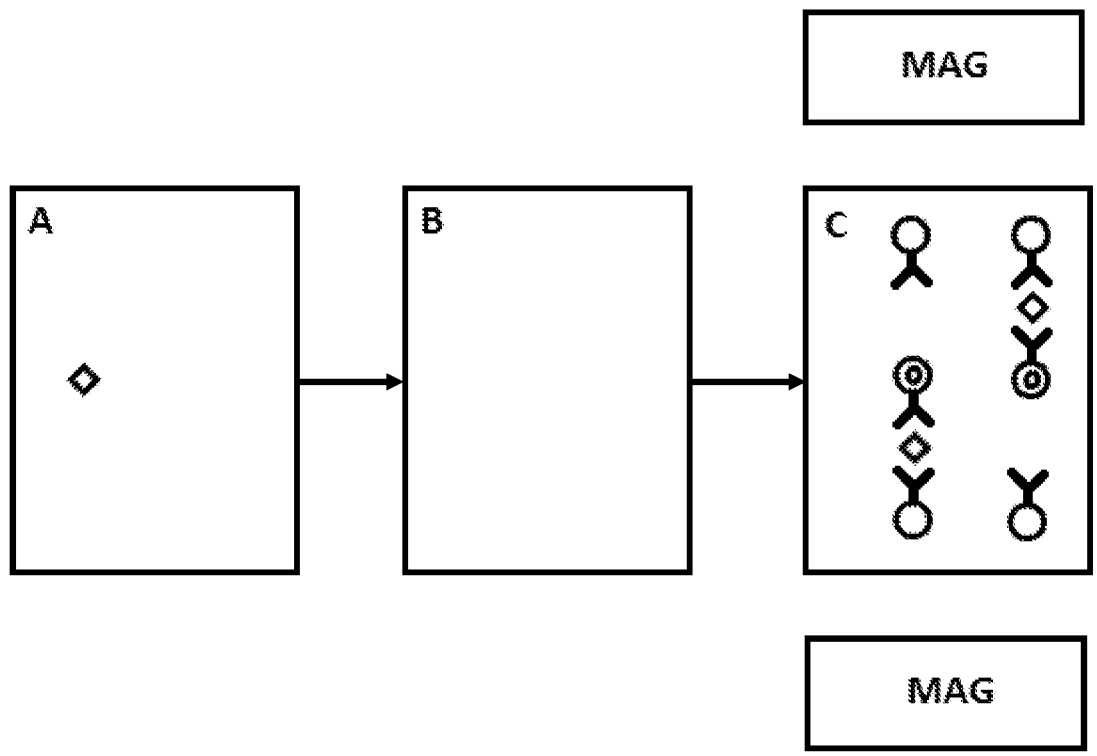
FIG. 5 depicts the detection reaction for the scheme of FIG. 4.
Figure 6:
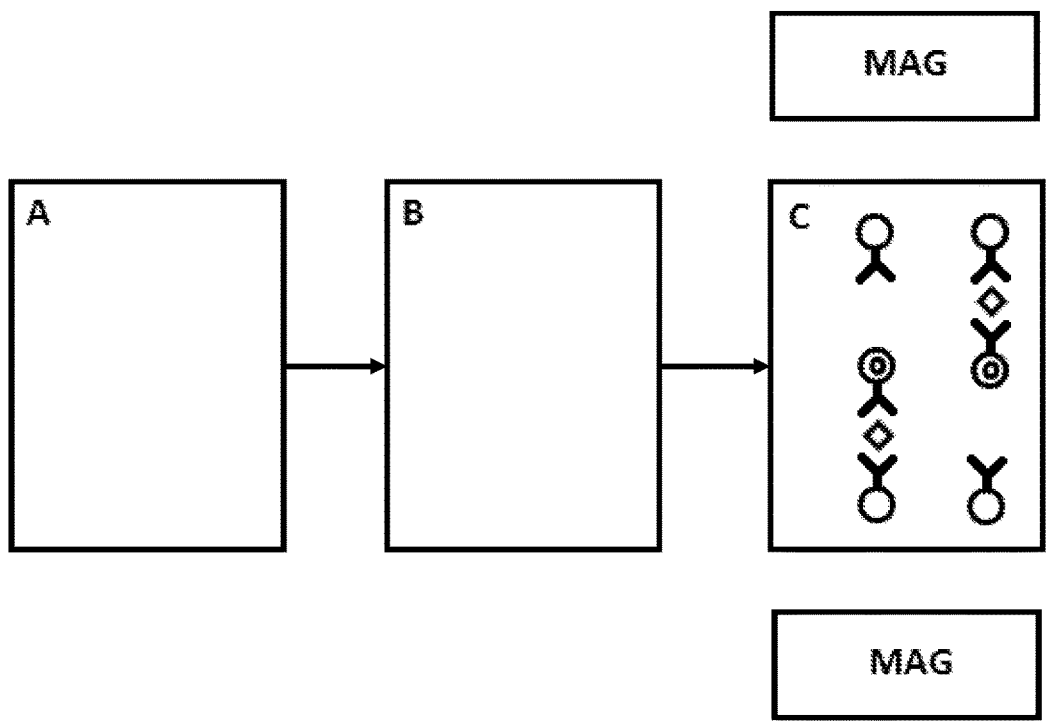
FIG. 6 illustrates movement to the right in Region C using where silver nanoparticles are under pressure from generated gas.
Figure 7:
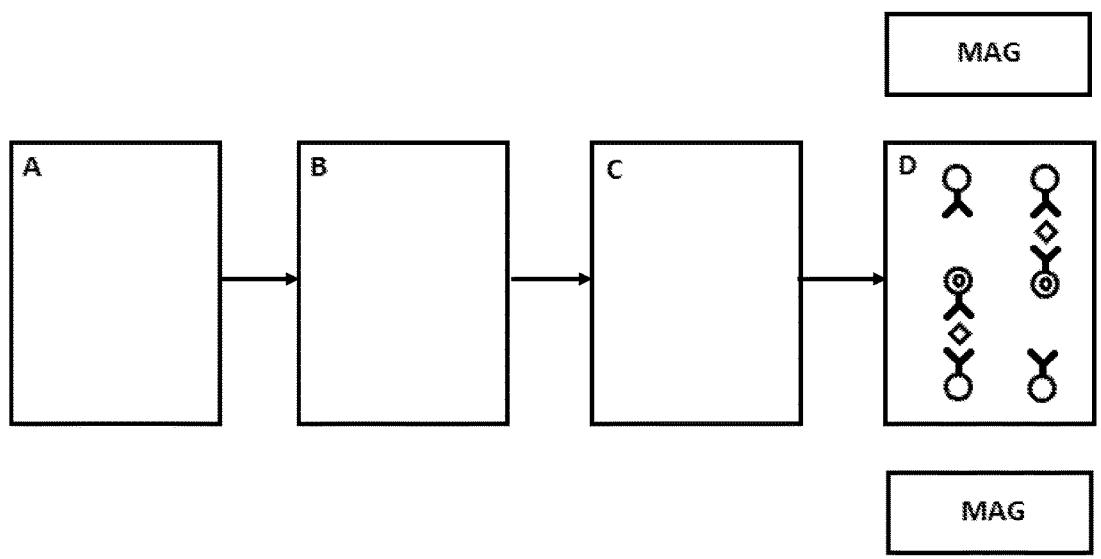
FIG. 7 demonstrates termination of a catalytic reaction in a new Region D.

In particular aspects of the disclosure, a sample is provided to the device, and the sample thereby may enter a region that has or does not have magnetic particles with a primary antibody. The magnetic particles may be moved into a sample region. Once the sample is in the region with the magnetic particles, the analyte from the sample, if present in the sample, is able to bind to the antibody on the magnetic particles (see FIGS. 3 and 4). Once the analyte is bound to the antibody on the particle, the magnet may move the particles to another region harboring nanoparticles with a secondary antibody (FIG. 5) or an enzyme with a secondary antibody. Upon binding of the magnetic particle/primary antibody/antigen to the secondary antibody/nanoparticles or secondary antibody/enzymes, the complexes are moved to a detection region of the device by the magnets. The detection region comprises particular detection reagents based on the desired detection assay. In an example case wherein the enzyme/secondary antibody complex comprises catalase, the detection region comprises hydrogen peroxide such that oxygen that is produced (FIG. 6) is detected (for example by movement of the boundary of the detection region from pressure of the oxygen (FIGS. 7 and 8). The complexes may be moved to yet another region for termination of the catalytic reaction (FIG. 8).

Figure 12:
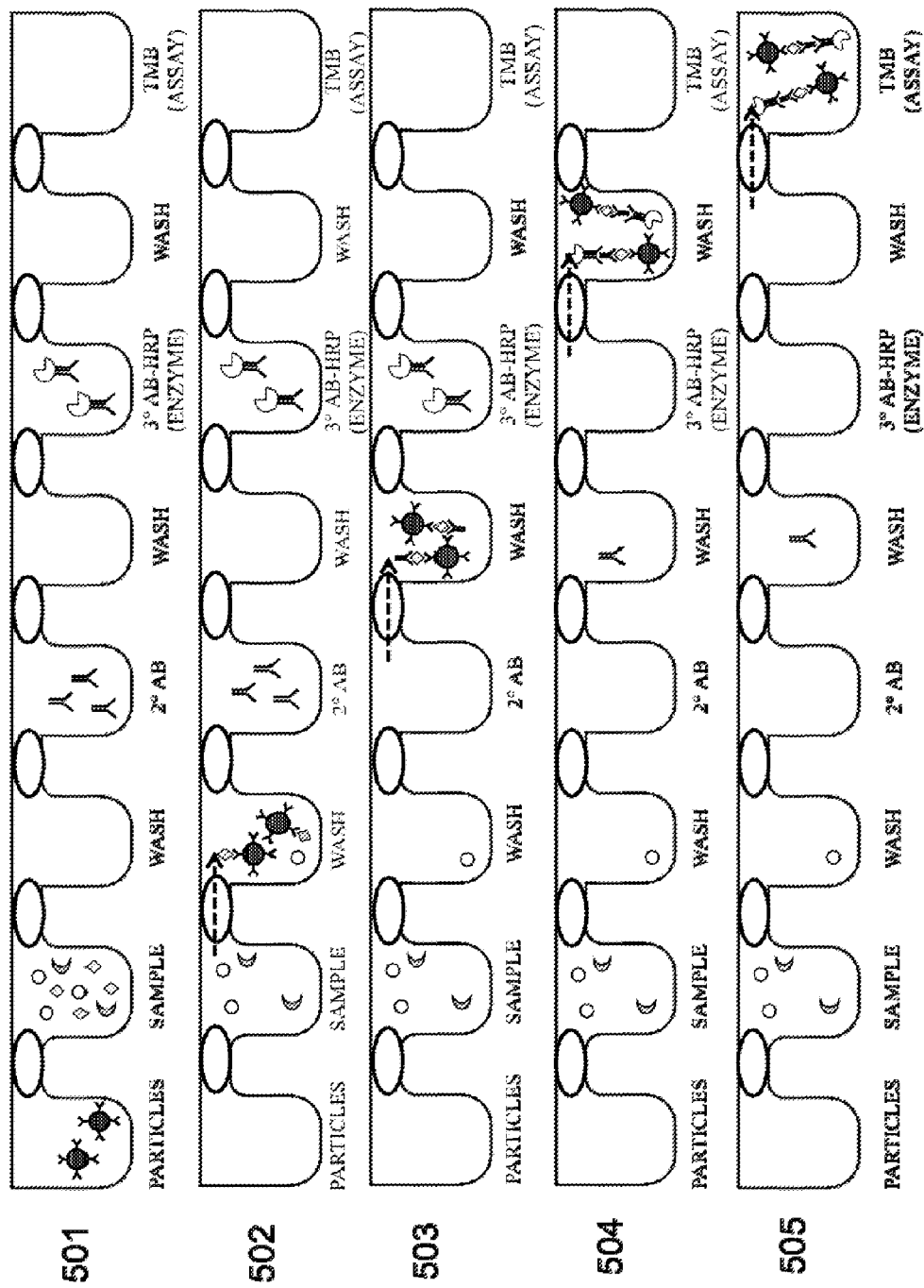
FIG. 12 shows illustrations of each step of the movement of magnetic particles through fluidic compartments, and the subsequent binding and enzymatic reactions that take place in a sequential manner aided only by the controlled movement of external magnets.

In the card version of the device the chambers may be loaded using micropipettes or syringes, for example, and then sealed. The sample is loaded in the sample chamber. In the tube version, withdrawal of a plunger, such as a wire plunger, may be used to draw liquids into the capillary. One end of the capillary is dipped into the solution of choice and the wire is withdrawn to the desired length to draw in the liquid by suction. The sample may also be loaded through capillary action. FIG. 12 shows an embodiment of the use of a discontinuous fluidic system to perform an ELISA immunoassay. Element 501 shows a method in which the different chambers can be filled with different liquids and magnetic particles. The antibody coated particles are then dragged across the air gap to interact with the loaded sample before being moved to the next chamber (502). This adds the sample analyte to the antibodies. The particles are then sequentially moved across the secondary antibodies (503) and tertiary, enzyme-bound, antibodies (504) before finally ending up in the chamber containing the substrate for the enzyme (505) which changes color. This embodiment also shows the optional wash chambers to remove contaminants attached non-specifically to the particles.

In the card, the sample, reaction and detection regions are connected by thin empty channels. In an exemplary embodiment, air gaps are used. Gaps can also be filled by any gas, or water-immiscible viscous liquids, such as mineral oils. One exemplary embodiment of the order of regions is as follows from the sample loading point: sample+magnetic particles→gap→silver nanoparticles/enzymes→gap→hydrogen peroxide/TMB→gap, where gap is defined as the space between the regions (the gap may be about 1 mm to 15 mm, in some cases). In the tube version, the plunger is pushed in to eliminate the fluid matrix that was harboring the magnetic particles, while leaving the particles on the wall of the capillary. The open tip of the capillary is dipped into the test solution containing the analyte. The plunger is withdrawn slowly, drawing in the test solution into the region containing the magnetic particles attached to the walls by the magnetic field.

The magnet is moved forward slowly using an external magnetic field, dragging the magnetic beads (such as along the capillary wall), across the air-gap or other fluid gap and into the second region (see FIG. 12, for example). This can be either in the form of movement of permanent magnets or in the form of a varying electromagnetic field.

In an exemplary embodiment, multiple permanent magnets arranged in parallel produce parallel magnetic fields that control the movement of magnetic particles through multiple parallel fluid device channels, allowing replicates and/or simultaneous controls of the immunoassay to be performed in tandem in a single cycle of the disclosed method.

After a reaction time in the second region, the magnet is again used to draw the magnetic particles into and through the next gap, and thence to the region containing the detecting chemical.

When using horseradish peroxidase (HRP) and TMB, the action of the enzyme on the substrate causes a change in color. When using chemiluminescent chemicals and HRP, light is generated. When using silver nanoparticles and hydrogen peroxide, the strong catalytic action of silver on hydrogen peroxide causes a breakdown and release of oxygen. Within the sealed capillary space, the released oxygen increases fluid pressure and moves all the chemicals, including the silver nanoparticles, towards the open end of the capillary.

After a suitable reaction time (for example, 2-10 minutes) the particles are moved from the reaction region to the final gap, thereby terminating the catalytic reaction (FIG. 8). The concentration of analyte in solution is proportional to the amount of the analyte that gets attached to the antibody-coated magnetic particles, which in turn is proportional to the number of secondary antibody molecules that get attached to the analyte. Because the secondary antibodies are attached to catalysts (silver nanoparticles/HRP), this dictates the rate of catalytic breakdown of the hydrogen peroxide/TMB. The color concentration can be quantified with a light source and detector, for example. The oxygen generated moves the silver region proportionately, and this displacement of the silver nanoparticle region is a representation of the concentration of the analyte in solution.

Although the present invention and its advantages have been described in detail, it should be understood that various changes, substitutions and alterations can be made herein without departing from the spirit and scope of the invention as defined by the appended description. Moreover, the scope of the present application is not intended to be limited to the particular embodiments of the process, machine, manufacture, composition of matter, means, methods and steps described in the specification. As one of ordinary skill in the art will readily appreciate from the disclosure of the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended descriptions are intended to include within their scope such processes, machines, manufacture, compositions of matter, means, methods, or steps.

The disclosure of all patents and publications cited herein are hereby incorporated by reference in their entirety.

REFERENCES CITED

Neurauter A A et ai, Adv Biochem Eng Biotechnol. 2007; 106:41-73.

Sittampalam G S et al Assay Guidance Manual [Internet].

What is claimed is:

1. A method of detecting an analyte in a control or sample solution in a fluidic device, said device including a plurality of chambers separated by channels having an air-gap, comprising the steps of:
   contacting a sample solution in a first chamber of said device with magnetic particles, wherein said magnetic particles comprise a primary binding agent that binds to an analyte in the sample solution; and wherein the first chamber comprises two opposed parallel walls;
   moving the magnetic particles under the influence of a magnetic field from the first chamber and into a first channel having an air-gap therein, wherein the first channel comprises a lower wall which is aligned substantially transverse to the opposed parallel walls of the first chamber, and wherein an upper portion of one wall of the first chamber adjacent to the first channel transitions as a curve bending towards the lower wall of the first channel;
   moving the magnetic particles under the influence of the magnetic field across the air-gap in the first channel and into a second chamber comprising two opposed parallel walls, wherein an upper portion of one wall of the second chamber is adjacent to the first channel and is also substantially parallel where it meets the lower wall of the first channel, and wherein the second chamber contains a second solution comprising a detection binding agent which is capable of binding to the analyte or to the primary binding agent;
   removing unbound sample solution by passing the magnetic particles across the air-gap in the first channel;
   moving the magnetic particles under the influence of the magnetic field through a second channel and across the air-gap therein and into a third chamber, wherein the third chamber contains an indicator capable of generating a signal indicating the presence of the detection binding agent;
   removing unbound sample solution and second solution by passing the magnetic particles across the air-gap in the second channel; and
   detecting the signal, wherein the presence of signal indicates analyte in the sample solution and the intensity of signal correlates with the quantity of analyte in the sample solution;
   but wherein the magnetic particles are not moved to a wash chamber which contains solution capable of removing unbound reactants, as there is no such wash chamber in the fluidic device.

2. The method of claim 1 wherein the binding agents are one or more of: proteins, antibodies, peptides, aptamers, chemical moieties or nucleic acids.

3. The method of claim 1 wherein the primary binding agent is an antibody, and the analyte is an antibody or an antigen.

4. The method of claim 1 wherein the primary binding agent is an antigen, and the detection binding agent binds to an antibody which binds to the antigen.

5. The method of claim 1 wherein the plurality of chambers and the channels are contained in a cartridge.

6. The method of claim 5 wherein the cartridge is marked with an identifier that is capable of being read by a sensor or sensor camera for robotic or computational automation.

7. The method of claim 6, wherein the identifier is a quick response code (QR-code) or bar code.

8. The method of claim 1 wherein the magnetic field is generated by permanent magnets which are moved in a linear path under external control.

9. The method of claim 8 where the movement of the permanent magnets is programmed.

10. The method of claim 9 further including moving the magnetic field in a second direction.

11. The method of claim 10 wherein the second direction is transverse to the linear path.

12. The method of claim 1 wherein movement of the magnetic field is varied in order to enhance movement of the magnetic particles in a desired direction.

13. The method of claim 1 wherein a light source and a detector are used to record the signal.

14. The method of claim 1 wherein the signal intensity is determined by examining and comparing the signal from pixels within an image.

15. The method of claim 1 wherein the signal is in the form of color, fluorescence, luminescence, or radioactivity.

16. The method of claim 15 wherein a color change is mediated by one or more of the following: PNPP (p-Nitrophenyl Phosphate), ABTS (2,2'-Azinobis [3-ethylbenzothiazoline-6-sulfonic acid]diammonium salt), OPD (o-phenylenediamine dihydrochloride), and TMB (3,3',5,5'tetramethylbenzidine).

17. The method of claim 16 wherein TMB is reacted with horseradish peroxidase to generate the color change.

* * * * *